(12) United States Patent
Ruegg et al.

(10) Patent No.: US 6,626,824 B2
(45) Date of Patent: Sep. 30, 2003

(54) EXCHANGEABLE TOOL ASSEMBLY FOR AN ENDOSCOPIC TREATMENT DEVICE AND SUCH TREATMENT DEVICE

(75) Inventors: Thomas Ruegg, Schaffhausen (CH); Beat Krattiger, Beringen (CH); Harald Haan, Schaffhausen (CH)

(73) Assignee: Storz Endoskop GmbH (CH)

( * ) Notice: Subject to any disclaimer, the term of this patent is extended or adjusted under 35 U.S.C. 154(b) by 0 days.

(21) Appl. No.: 09/859,199

(22) Filed: May 16, 2001

(65) Prior Publication Data

US 2002/0013570 A1 Jan. 31, 2002

(30) Foreign Application Priority Data

May 16, 2000 (DE) .......................................... 100 23 685
Sep. 14, 2000 (EP) ............................................ 00119988

(51) Int. Cl.[7] ................................................. A61B 1/00
(52) U.S. Cl. ....................................... 600/104; 600/106
(58) Field of Search ............................ 606/1, 170, 171, 606/180, 79, 80, 81, 82, 83; 600/104, 106, 568; 604/22; 433/127, 128, 112, 114; 356/241.4

(56) References Cited

U.S. PATENT DOCUMENTS

| | | | | |
|---|---|---|---|---|
| 5,286,253 A | * | 2/1994 | Fucci ........................... | 604/22 |
| 5,320,627 A | * | 6/1994 | Sorensen et al. ............ | 600/564 |
| 5,695,506 A | * | 12/1997 | Pike et al. .................... | 606/159 |
| 5,928,241 A | * | 7/1999 | Menut et al. ................. | 279/143 |
| 5,957,945 A | * | 9/1999 | Bays ............................ | 604/22 |
| 6,000,940 A | * | 12/1999 | Buss et al. ................... | 433/127 |
| 6,010,476 A | * | 1/2000 | Saadat .......................... | 604/22 |
| 6,059,719 A | * | 5/2000 | Yamamoto et al. .......... | 600/104 |
| 6,068,641 A | * | 5/2000 | Varsseveld .................... | 606/170 |
| 6,368,324 B1 | * | 4/2002 | Dinger et al. ................ | 606/171 |

* cited by examiner

Primary Examiner—Linda C. M. Dvorak
Assistant Examiner—Kenneth G Schopfer
(74) Attorney, Agent, or Firm—St. Onge Steward Johnston & Reens LLC

(57) ABSTRACT

An exchangeable tool assembly is provided for an endoscopic treatment device, comprising a flexible shaft connected at its distal end to a tool unit and at its proximal end to a coupling element for coupling the tool assembly to a motor of the treatment device. The flexible shaft transmits a rotary movement of the motor to the tool unit. The flexible shaft is connected to said tool unit such that said flexible shaft and said tool unit form a jointly exchangeable unit. Further, a locking mechanism for releasably holding said tool assembly at said treatment device comprises a locking element arranged at said tool unit and a locking member arranged at said treatment device which is engageable in said locking member to releasably hold said unit formed by said tool unit and said flexible shaft at the treatment device, which can be withdrawn as a whole after this engagement of said locking member from said locking element.

17 Claims, 5 Drawing Sheets

EXCHANGEABLE TOOL ASSEMBLY FOR AN ENDOSCOPIC TREATMENT DEVICE AND SUCH TREATMENT DEVICE

CROSS-REFERENCE OF PENDING APPLICATIONS

This application claims priority of German application 10023685.5 filed May 16, 2000 and European application 00119988.4 filed Sep. 14, 2000, both applications are pending.

BACKGROUND OF THE INVENTION

The invention relates to an exchangeable tool assembly for an endoscopic treatment device, comprising a flexible shaft connected at its distal end to a tool unit and at its proximal end to a coupling element, and further comprising a locking mechanism to releasably hold the tool assembly at the treatment device.

Further, the invention relates to an endoscopic treatment device with an afore-mentioned tool assembly.

A tool assembly and a treatment device of the afore-mentioned kind are known from U.S. Pat. No. 5,349,940.

Such an endoscopic treatment device can be used in technical applications, in the medical field, in particular in the field of minimally invasive surgery, and also in dental medicine or dental techniques.

In technical applications a treatment carried out with the treatment device includes, for example, removing burrs from forged pieces, grinding notches in turbine blades, grinding off corrosion for surface analysis, for example crack testing, grinding off welding seams, boring holes, etc. In minimally invasive surgery such a treatment device can be used to treat tissue in the body through a small incision, for example for excising tissue.

In general such an endoscopic treatment device is intended to be used for universal endoscopic treatments and/or analysis under visual control, mainly with a rotating tool, at difficultly accessible locations.

In known rigid devices, the transmission of motion from the proximally located motor to the distally located working tool is accomplished with a rigid drive shaft or with transmission belts. These transmission belts require gears and deflection rollers, which lead to losses in space and efficiency. The construction of the power transmission from the proximal motor to the distal working unit is complicated and subject to disturbance. Rigid drive shafts lying parallel and close to the longitudinal axis of the working shaft cannot be coupled directly to the motor, because the motor has certain minimal dimensions which obstruct the fixed optic lenses. However, this would not be the case with fiber optics, which, however, has less resolution.

Flywheel forces and imbalances, which can occur in use of the endoscopic treatment device at the tool unit and at the transmission element in form of the flexible shaft lead to vibrations which cause an upper limit to the rotary speed. The lower speeds resulting from this construction lead to a reduction in removal or excising capacity.

Furthermore, it is not only the distally located tool unit which is subject to wear in such a treatment device, but also the flexible shaft and the coupling of the flexible shaft to the motor. Treatment devices are known, where the tool unit and the flexible shaft and the coupling element cannot be exchanged or at least not simply, as it is, for example, the case with the tool assembly known from U.S. Pat. No. 5,349,940, whereby maintenance of such treatment devices is very cost intensive.

Medical devices are known which must be operated with flushing fluid to lubricate the bearings. Such a treatment device is therefore not usable in technical applications. The exchangeable tool assembly contains all of the wearing elements such as bearings, the working head as well as the shaft and shaft protector. However, it is rigid and due to its construction it is not designed for higher rotary speeds.

From the document U.S. Pat. No. 5,349,940 mentioned at the outset an endoscopic treatment device is known, comprising an exchangeable tool assembly, wherein the tool assembly comprises a flexible shaft, which is connected at its distal end to a tool unit and at its proximal end to a coupling element. The tool unit comprising the working head, for example a milling head, is releasably connected to the flexible shaft via a screw and plug coupling so that the coupling between the tool unit and the shaft must be released at first in order to exchange the tool unit. The flexible shaft itself comprises a plurality of parts and exchange and mounting of the shaft to the device is difficult. The connection between the tool unit, the flexible shaft and the motor therefore consists of a plurality of parts, i.e. several single parts must be fitted, plugged and screwed together, whereby the exchange of this known exchangeable tool assembly and, thus, the maintenance of the treatment device is complicated.

It is, therefore, an object of the present invention to improve an exchangeable tool assembly for an endoscopic treatment device mentioned at the outset as well as to provide such a treatment device, such that the tool assembly can be simply and quickly exchanged, wherein all parts subject to wear are exchangeable with low expenditure of handling.

SUMMARY OF THE INVENTION

According to the present invention, this object is achieved with an exchangeable tool assembly for an endoscopic treatment device, comprising:

a tool unit;

a coupling element for coupling said tool assembly to a motor of said treatment device;

a flexible shaft having a distal end and a proximal end, said distal end being connected to said tool unit and said proximal end being connected to said coupling element, said flexible shaft transmitting a rotary movement of said motor to said tool unit, said flexible shaft being connected to said tool unit such that said flexible shaft and said tool unit form a jointly exchangeable unit; and a locking mechanism for releasably holding said tool assembly at said treatment device, said locking mechanism comprising a locking element arranged at said tool unit and a locking member arranged at said treatment device, which is engageable with said locking element to releasably hold said jointly exchangeable unit formed by said tool unit and said flexible shaft, which can be withdrawn as a whole after disengagement of said locking member from said locking element.

Further, according to the present invention, an endoscopic treatment device is provided with an exchangeable tool assembly according to the present invention.

The afore-mentioned connection between the tool unit and the flexible shaft is advantageous as to a simple exchange of the exchangeable tool assembly, because these two elements subject to wear can be exchanged as an integral unit and thus in an easily handable manner, because they have not to be connected to one another for exchange. Furthermore, this configuration advantageously makes it possible to configure the tool unit and the flexible shaft in miniaturized form, whereby very high rotary speeds of the tool assembly are possible, without vibrational dampening measures, such as dynamic balancing, dampening and friction-reducing measures being additionally necessary. Such a miniaturization cannot be envisaged with the exchangeable tool assembly known from U.S. Pat. No. 5,349,940 because of its constitution of multiple parts. According to the present invention, the locking mechanism is configured such that locking of the tool assembly, i.e. the integral unit consisting of the tool unit and the flexible shaft, can be accomplished by means of a locking element arranged at the tool unit, in which a locking member of the treatment device engages. The flexible shaft is then axially immobilized at the treatment device through the locking of the tool unit.

The connection between the flexible shaft and the tool unit can be realized by assembling, for example by soldering or welding, or the tool unit can be connected to the flexible shaft in one piece or in monolithic fashion.

In a preferred embodiment the flexible shaft is connected to the proximal coupling element such that the coupling element can be withdrawn together with the flexible shaft and the tool unit after releasing the locking mechanism.

In this embodiment the tool unit, the flexible shaft as well as the coupling element and thus all parts subject to wear are exchangeable in simply handable manner, and for immobilizing this unit at the treatment device only the aforementioned locking mechanism comprising the locking element arranged at the tool unit and the locking member arranged at the treatment device is to be manipulated.

The locking mechanism according to the present invention having a locking member of the treatment device engageable into a locking element of the tool unit represents a quickly releasable and quickly lockable locking mechanism, which essentially simplifies the exchange of the exchangeable tool assembly. As already mentioned all parts subject to wear are integrated in one exchangeable element, whereby handling of the exchange is simplified and furthermore, the costs of the exchangeable tool assembly are reduced with respect to the manufacturing expenditure.

In a further preferred embodiment the tool unit comprises a working head and a tool shaft, and said locking element is configured as an annular groove in that tool shaft.

When the working head and the tool shaft rotate, the locking member engaging in the groove axially secures the exchangeable tool assembly. The advantages of this measure are that a constructively very simple locking mechanism is achieved, which can be realized in a simple production operation, namely by machining the circumferential annular groove at the tool shaft. Such a locking mechanism has the further advantage that locking is achieved with a minimal requirement on additional shaft diameter. By locking the tool assembly in its distal region, namely at the tool unit, a good tool guidance with the flexible shaft is made possible. If the tool assembly were locked proximally at the motor coupling, the tool unit when subjected to axial force would be deflected proximally due to the spring action of the flexible shaft. Thereby, handling of the tool would be rendered inaccurate.

In a further preferred embodiment a bearing bush is provided which receives an axial portion of the tool shaft and has a slot configured such that the locking element can pass through the slot.

This measure has the advantage that the rotating tool and the bearing bush are simultaneously locked by the locking mechanism. The bearing bush can be withdrawn from the treating device when the tool assembly is withdrawn, and can be exchanged as a part subject to wear. As will be described later on the bearing bush has a slight radial play in the treatment device.

In a further preferred embodiment the flexible shaft is configured as a braided cable, or as a profile in form of a wire, tube or angular profile.

These measures represent advantageous configurations of the flexible shaft, in order to impart a certain flexibility thereto. With a flexible shaft, the tool assembly can be also used in such treatment devices, which comprise a flexible working shaft in order to reach difficultly accessible working areas. With a configuration of the flexible shaft as a hollow profile, the shaft can also be used for transportation of material, signals or information to the working head of the tool unit and therefrom.

In a further preferred embodiment the flexible shaft is made from a highly flexible alloy.

Such highly flexible alloys can be Nitinol® or Tinel®.

In a further preferred embodiment a spiral is provided which rotatably receives an axial portion of the flexible shaft.

With the spiral surrounding the flexible shaft, with a play least possible and not rotating therewith, a stabilizing rigidity can be given to the flexible shaft despite its flexibility, and imbalances cannot build up. Imbalance would lead to disturbing vibrations and to frictional losses on the inner side of the spiral.

In this context it is preferred if a mantle, preferably a plastic mantle is provided surrounding the spiral.

The plastic mantle advantageously serves as a vibration damper. Resonance are eliminated by damping which when combining the vibrations could lead to frictional losses. Furthermore, the plastic mantle advantageously protects the spiral against deformations which could arise in assembly or disassembly. Furthermore, it prevents lubricant loss.

A treatment device according to the present invention comprises a tool assembly according to the present invention according to one or more of the afore-mentioned embodiments.

In this context, it is preferred, when the locking member extends perpendicularly to a longitudinal axis of the device and at its end opposite to the longitudinal axis is attached to a holding part of the locking mechanism running parallel to the longitudinal axis.

Further, it is preferred, if the holding part is configured as a biased bracket urged substantially perpendicularly to the longitudinal axis, so that the locking member is movable perpendicularly to the longitudinal axis.

This configuration of the locking mechanism having the locking member arranged at the holding part configured as an elastically biased bracket has the advantage that locking as well as releasing is very easy to handle, in particular, the locking member automatically disengages from the locking element at the tool unit on release of the locking mechanism.

In this context, it is further preferred if the locking mechanism comprises a sleeve displaceable in axial direction, which is configured to be slideable over the bracket and moves the locking member perpendicularly to the longitudinal axis, so that the locking member engages in the locking element of the tool assembly.

Altogether, the locking mechanism according to the present invention has the advantage that no screws have to be tightened or to be released for exchanging the tool assembly, but only the slide sleeve must be displaced in proximal direction whereby the biased bracket with the locking member arranged thereon automatically resiliently moves aside, whereby the locking member disengages from the locking element, and must be displaced in distal direction for locking, whereby the slide sleeve urges the bracket radially inwardly so that the locking member engages the locking element.

In a further preferred embodiment an insert channel is provided which receives the tool assembly, wherein the tool assembly can be introduced into and removed from the insert channel in axial direction, and wherein the tool assembly is received in the insert channel with radial play.

This play has the advantageous effect that imbalances of the tool unit do not have a strong effect. In the region of the bearing bush this measure has the effect that imbalances do not have a strong effect, but are compensated by a minimal movement of the bearing bush. This self-balancing increases the lifetime, because the vibrations caused by friction are minimized. In the region of the flexible shaft this play also has the advantage that the shaft is slightly moved by the imbalances whereby a self-balancing arises which minimizes the vibrations.

In a further preferred embodiment the treatment device comprises a working shaft, in which the insert channel and parallelly thereto a channel for an endoscope is arranged.

In a further preferred embodiment the working shaft comprises in its distal region a flexible part for deflecting the tool unit with respect to a longitudinal axis portion of a proximal region of the working shaft.

By this measure difficultly accessible working regions can be endoscopically treated or analyzed, and the motor rotation can be transmitted through the bend to the tool unit via the flexible shaft.

Further advantages will be apparent from the following description and the attached drawings.

It is to be understood that the features mentioned above and those yet to be explained below can be used not only in the respective combinations indicated, but also in other combinations or in isolation, without leaving the context of the present invention.

The invention will be explained and described in more detail below with reference to selected exemplifying embodiments in conjunction with the attended drawings.

DETAILED DESCRIPTION OF PREFERRED EMBODIMENTS

Figure 1A:
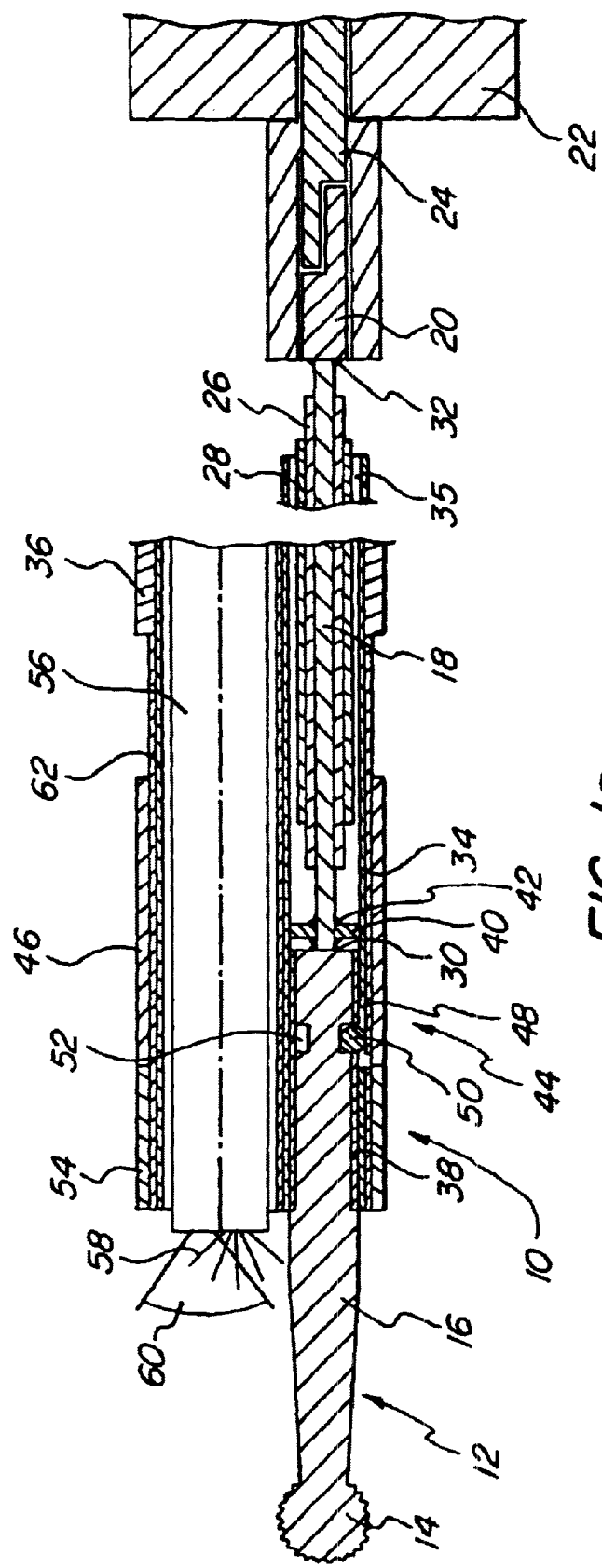
FIG. 1a shows a longitudinal sectional view of a working shaft of a treatment device with an exchangable tool assembly in its state locked at the treatment device.
Figure 1B:
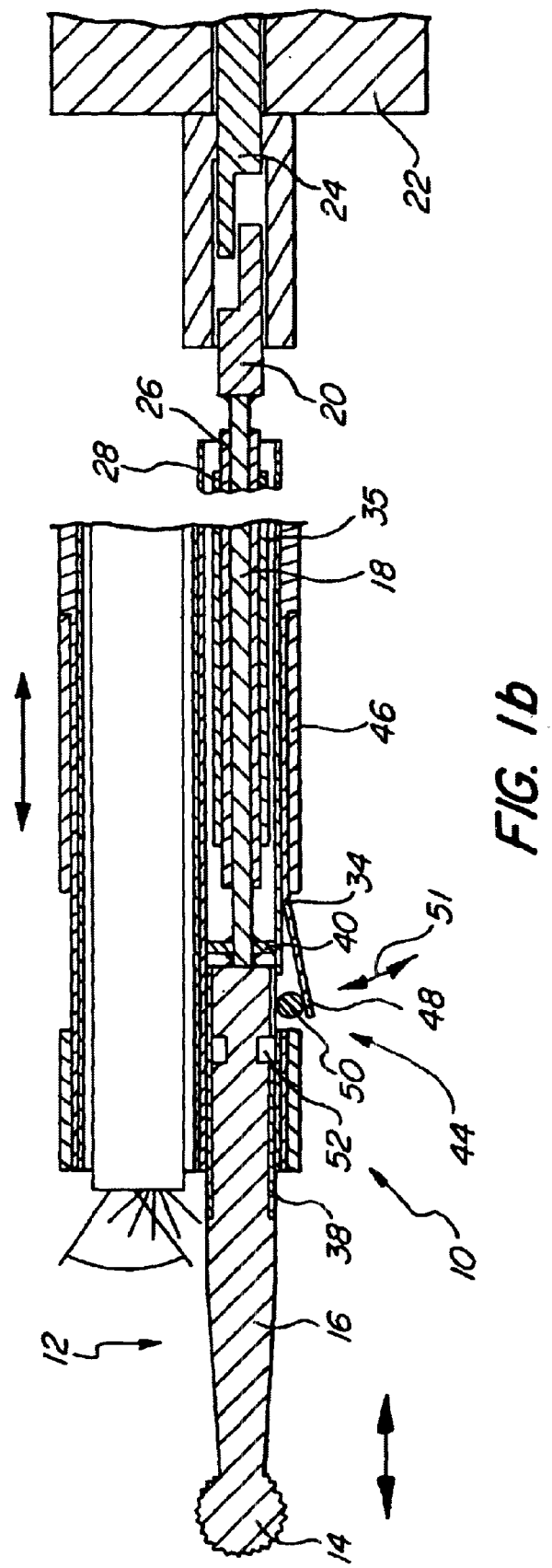
FIG. 1b shows a representation similar to FIG. 1a) showing the tool assembly in a state released from the treatment device.
Figure 2:
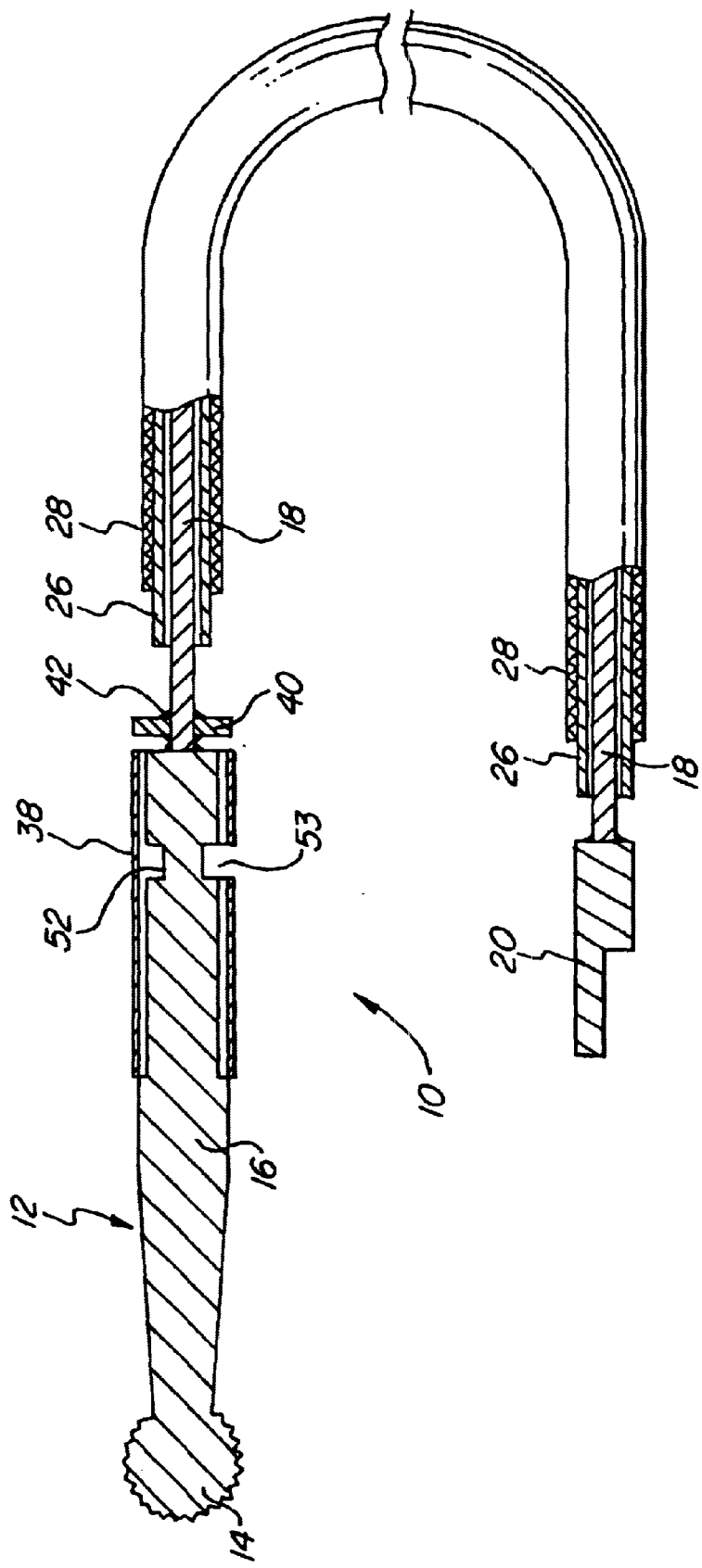
FIG. 2 shows a side view of the exchangeable tool assembly in FIG. 1, partially in longitudinal sectional representation, withdrawn from the treatment device in a curved state.

With reference to FIGS. 1 and 2 an exchangeable tool assembly 10 is described hereafter, which is used in an endoscopic treatment device according to FIGS. 3 and 4 to be discussed below.

In FIG. 1, the exchangeable tool assembly 10 is shown in a state inserted in a treatment device, and is shown alone and in a curved state compared with FIG. 1 in FIG. 2.

The exchangeable tool assembly 10 and the endoscopic treatment devices to be discussed below can be used in technical applications, medical applications, in particular in the minimally invasive surgery or in the dental medicine or dental techniques as well.

The cost effectively produceable tool assembly 10 in a realized embodiment comprises a tool unit 12, which comprises a working head 14, for example a grinder, miller, etc. and a tool shaft 16, for example for use in dental technology.

At the proximal end of the tool shaft 16 a flexible shaft 18 in form of a braided cable made of steel is connected to the tool unit 12, for example by means of a soldering 30, and forms with the tool unit 12 an integrated unit. On one hand the braided cable is more flexible than a solid wire, while on the other hand the braided cable dampens crossvibrations arising from an imbalance.

The tool unit 12 is proximally connected to a coupling element 20 via the shaft 18 as to form an integrated unit therewith, in that the shaft 18 is connected with its proximal end by means of a soldering 32 for example, to the coupling element 20. The coupling element 20 forms the releasable connection of the tool assembly 10 to a motor 22, exactly spoken to the motor shaft 24 thereof.

The tool unit 12, the shaft 18 and the coupling element 20 form a jointly exchangeable integral unit, which can be instead of being soldered together be made in one piece.

The shaft 18 is surrounded by a non-rotating spiral 26. Between the spiral 26 and the shaft 18 is provided the smallest possible play so that no imbalance can build up. An imbalance would lead to disturbing vibrations and also to frictional losses on the inner side of the spiral 26. The spiral 26 itself is surrounded by a mantle, in particular a plastic mantle 28 in form of a shrink tube, which has several functions. Firstly, it serves as a vibration damper. Resonances are eliminated by the damping which when combining the vibrations could lead to frictional losses. Secondly, it protects the spiral 26 against deformations, which could arise in assembly or disassembly. Thirdly, it prevents lubricant loss.

Figure 3:
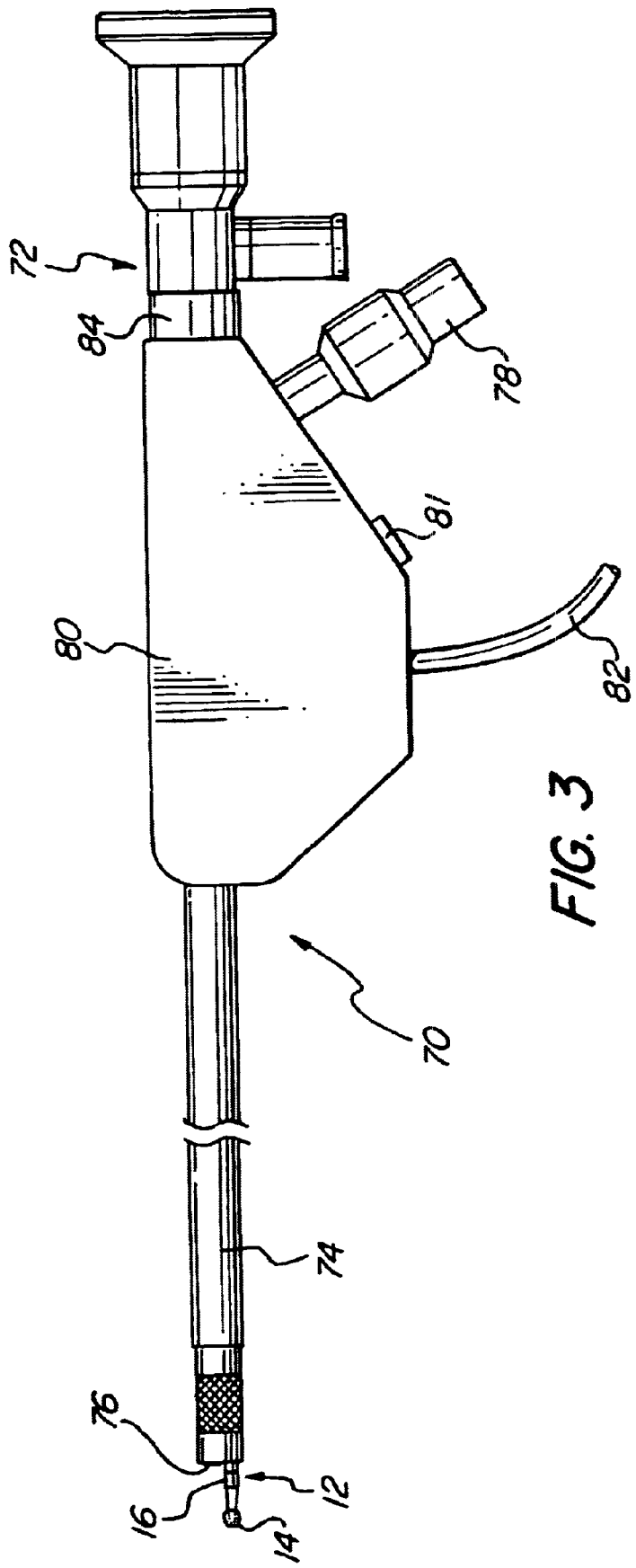
FIG. 3 shows a side view of an endoscopic treatment device having a rigid working shaft.
Figure 4:
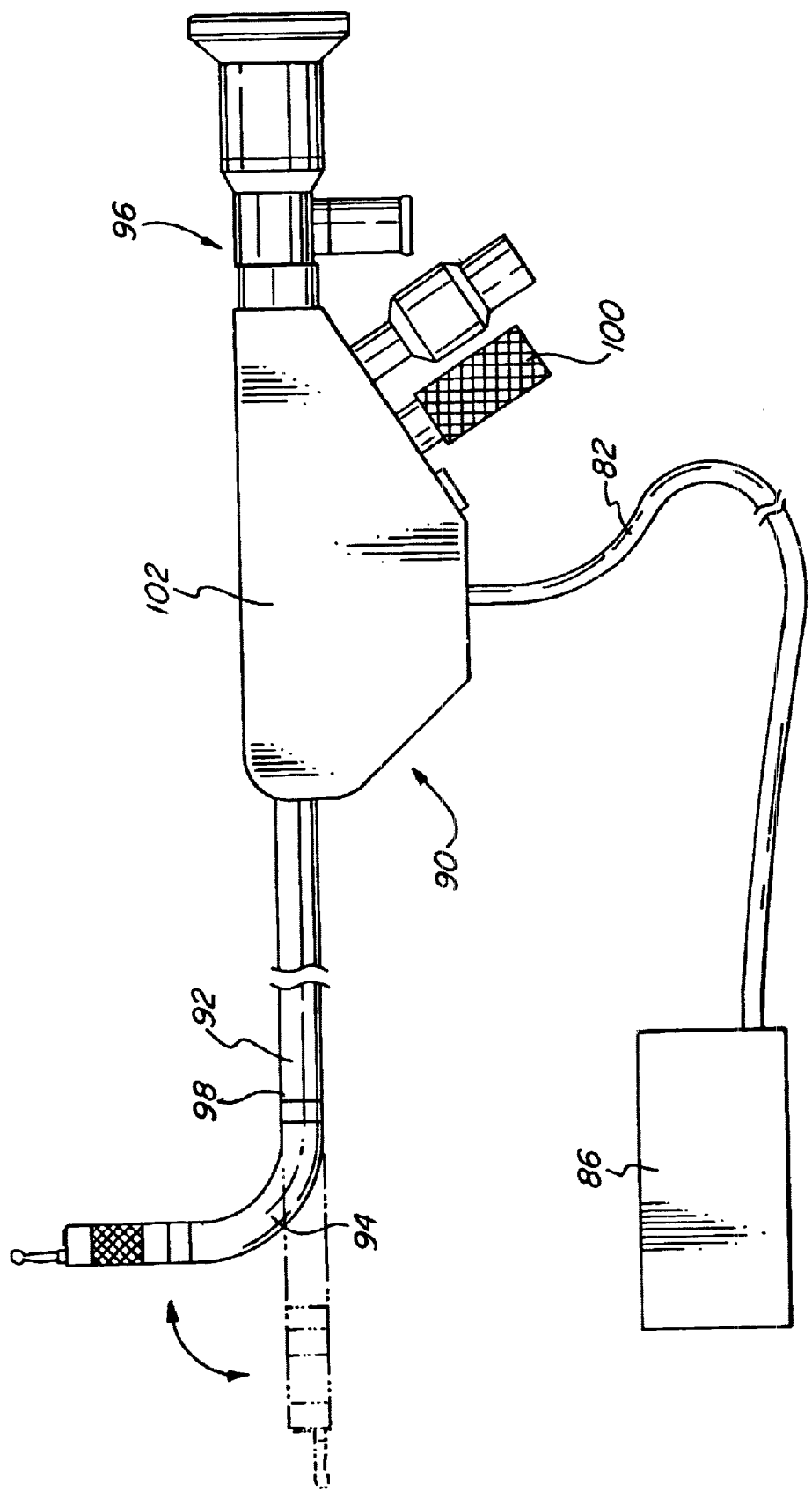
FIG. 4 shows a side view of an endoscopic treatment device having a flexible working shaft.

The tool assembly 10 is disposed in an insert channel 34 of a treatment device, like that represented in FIGS. 3 or 4, for example. The tool assembly 10 is received in the insert channel 34 with play.

The tool shaft 16 of the tool unit 12 is partially surrounded by a bearing bush 38. At the proximal side of the tool shaft 16 a holding disc 40 is fixed to the shaft 18, for example, by solderings 42. The holding disc 40 secures the bearing bush 38 against a sliding relative to the tool unit 12, in particular when the tool assembly 10 is removed from the treatment device, because, without the holding disc 40, the bearing bush 38 could get stuck in the distal end of the insert channel 34.

The bearing bush 38 is non-rotating.

In the distal region of the insert channel 34 a locking mechanism 44 is provided, anchoring the bearing bush 38 and therefore the entire exchangeable tool assembly 10. In the embodiment shown in FIG. 1 the locking mechanism 44 comprises a slide sleeve 46 in the distal region of the treatment device, which is disposed about the working shaft 36 of the treatment device. The slide sleeve 46 can be shifted in axial direction distally, as represented in FIG. 1a, and proximally, as represented in FIG. 1b. In the distally displaced position (FIG. 1a) the slide sleeve 46 locks the tool unit 12 having a locking element 52 in form of an annular circumferential groove therein, by urging an outwardly biased bracket to the inside, which has a locking member 50, and thereby axially immobilizes the tool unit 12, the shaft 18 and the coupling element 20 at the treatment device. The locking member 50 is configured in form of a tappet fixed to the bracket 48, which engages the groove forming the locking element 52 in the distal position of the slide sleeve 46, whereby the tool assembly 10 is axially immobilized at the treatment device. The locking mechanism 44 achieves locking with a minimal requirement on additional shaft diameter of the treatment device. The rotating tool unit 12 and the bearing bush 38 are axially locked simultaneously, the latter having a slot 53 therein, through which the tappet passes and engages in the annular groove of the tool shaft 16 for the purpose of locking.

In the proximally displaced position of the slide sleeve 46 (FIG. 1b) the bracket 48 resiliently springs outwardly and thereby disengages the locking member 50 from the locking element 52, as indicated by an arrow 51, whereafter the tool assembly 10, i.e. the unit comprised of the tool unit 12, the shaft 18 and the coupling element 20 can be jointly withdrawn from the insert channel 24. The holding disc 40 ensures that the bearing bush 38 is withdrawn from the insert channel 34 as well.

A distal end piece 54 at the distal end of the working shaft 36 serves as distal stop for the slide sleeve 46.

The bearing bush 38 has a slight play in the distal region of the treatment device, which has the effect that imbalances of the tool unit 12 do not have a strong effect, but are compensated by a minimal movement of the bearing bush 38. This self-balancing increases the lifetime, because the vibrations caused by friction are minimized.

A similar effect occurs with the shaft 18, i.e. the transmission element. The spiral 26 is slightly moved by imbalances in the shaft 18, i.e. in the braided cable. The movement is made possible by the play between the insertion channel and the plastic mantle 28 about the spiral 26. Through the slight movement dampened by the plastic mantle, a self-balancing arises which minimizes vibrations.

Since, as represented in FIG. 2, a transmission of movement must also be possible via the shaft 18 in curved form the bending modulus of the shaft 18 must be as small as possible to minimize friction.

The gyrating mass, which can vibrate, must be held low. The dimensions of asymmetries in the shaft 18 should be as small as possible. The relative surface speed between the shaft 18 and the plastic mantle 28 must be as small as possible. The area of a possible lubrication film about the shaft 18 must be held as small as possible.

The diameter of the shaft 18 is therefore important in many aspects with respect to frictional losses. The shaft 18 designed with the smallest possible diameter due to the above factors. Only a small torque need be transmitted, because the pressing forces of the working head 14 of the tool unit 12 are normally small. That is, the diameter of the shaft 18 should only be large enough such that the maximum torque of the motor 22 can be transferred.

The provision of self-balancing and vibrational damping of the tool assembly 10 allow high rotary speeds, for example above 30.000 rpm, without problem. In addition, the required motor rating is minimal, e.g. 2 watts, due to the miniaturization of the shaft 18, the tool unit 12 and the coupling element 20, which allows the use of a small motor and a sophisticated device design.

Instead of a braided cable, the flexible shaft 18 can also be configured as a profile, e.g. a wire, a tube or an angular profile, and in particular can be made from a highly flexible alloy like Nitinol®, or Tinel®.

Further embodiments of the invention for example make use of compressed air instead of electricity as the drive power for the motor 22, or for vibrational damping of the shaft 18, make use of a liquid bath in which the shaft 18 rotates.

Referring to FIG. 1, a channel 62 for guiding an endoscope 56 is present in the working shaft 36 of the treatment device besides the insert channel 34 and parallel thereto. In FIG. 1a the distal end of the endoscope shaft is represented only. The endoscope 56 includes a light supply (not shown) from the distal side of which illuminating light 58 emerges. The endoscope 56 further includes endoscope optics, in order to endoscopically observe a working area which also includes the working head 14 of the tool unit 12. The field of view of the endoscope optics is designated by reference numeral 60.

With reference to FIG. 3 a first embodiment of an endoscopic treatment device 70 having a rigid working shaft 74 is now described.

The working device 70 comprises a standard rigid endoscope or borescope 72 having a view direction of 0° to about 30°, which can be inserted in the working shaft 74 and locked via a bayonet lock 84. The working shaft 74 includes the insert channel 34 for the exchangeable tool assembly 10 according to FIG. 1.

In the exchangeable tool assembly 16 the wearing parts, such as the working head 14 (depending on the specific application), the bearing bush 38 and the flexible shaft 18, are collected to form an accessory assembly or unit, easily exchangeable by the user. Further universal working channels can be integrated into the working shaft 74. These can be used for probes (grasping forceps, driven or non-driven tools, sensors, additional light fibers, UV analysis light, UV curing light, laser treatment fibers, fiber optics for observation or spectroscopy, etc.) and/or media (adhesives, coatings, dyes, chemicals, coolants, lubricants, powder, compressed air, gas, water, etc.). The suctioning of material out of the treatment area is also possible (grinding dust, contaminations, sample removal for analysis).

The afore-mentioned working channels are preferably provided with a standard coupling connector 78, for example a Luer connector. Apart from supply lines, probes etc. can also be connected there. A view window 76 of the endoscope 72 lies approximately at the front face of the distal end of the working shaft 74. A handgrip housing 80 is provided at the proximal end of the working shaft 74, which contains the drive motor 22, switches 81, and electronics in its interior. The handgrip housing 80 further serves as a base for the securement and passage of the working channels mentioned before and a connector cable 82. The low weight and the form of the handgrip housing 80 allow an ergonomic holding of the handle. The length of the handgrip housing 80 however is as short as possible, which favors a longer working length.

The connector cable 82 is connected to a multifunctional supply unit 86 (shown in FIG. 4), which apart from supplying power (primarily electricity, but also compressed air is possible) for the motor 22 can also supply illumination light for the endoscope 72.

In operation, illumination light from a light source is passed through the light connector 73 into the endoscope 72. The light emitted from the distal end illuminates the cavity and the working head 14. The treatment device 70 operates with high rotary speeds, similar to a dental drill, which enables large removal capacities and exact guidance with small pressing forces.

The treatment device 70 can be activated either with the switch 81 on the handgrip housing 80 or with a foot switch (not shown). Preferably, the rotary speed can be adjusted to account for the tool unit 12 or the working head 14 and the working situation.

The direction of rotation is possible in both directions with certain flexible shafts 18 so that the direction of rotation can be chosen to account for the working situation. The rotation can also be intermitting and/or alternating if this is advantageous for example for a better precision and/or removal capacity.

The treatment device 70 can be guided under visual control through the endoscope 72 to the treatment location where the treatment can begin immediately.

The expensive endoscope 72 can be easily removed from the working shaft 74 at any time due to the modular construction. This is made possible by the easily releasable connection by means of the universal bayonet connection 84. The separated endoscope 72 enables a more precise inspection of the location to be treated, because the optics can be placed more closely to the surface for enlarged detail images, because the device is not held at a distance caused by the working head 14 of the tool assembly 10.

FIG. 4 shows a further embodiment of a treatment device 90 similar to the treatment device 70 in FIG. 3 so that only the differences are described in the following.

A working shaft 92 of the treatment device 90 is, compared with the working shaft 74 of the treatment device 70, provided with a flexible part or a linkage 94 so that the tool unit 12 with the working head 14 of the tool assembly 10 can be deflected. For reasons of mechanical stability, the deflection is preferably in one direction up to a predefined stop. When reaching the stop, the linkage is designed to abruptly become stiff. This stiffening improves the precise guidance of the tool unit 12. The deflection in only one direction still allows treatment in a large region in a cavity, because the treatment device 90 can also simply be rotated about its longitudinal axis. An endoscope 96 of the treatment device 90 according to this embodiment comprises, differently from the embodiment according to FIG. 3, a view direction of about 70°, wherein a view window 98 is provided before the linkage 94 by means of a corresponding opening in the mantle of the working shaft 92. The deflection of the distal end of the working shaft 92 in this embodiment is about 90°. The dimensions, the view direction and the view field (e.g. 30°) are coordinated such that the working head 14 lies at a suitable position in the image of the endoscope 96, e.g. in the center of the image or in the lower one-third, so that a suitable detail imaging of the surface to be treated is made possible. The angle of deflection and the view field, etc. are dependent upon the application.

The deflection of the distal end of the working shaft 92 is preferably achieved with a relatively small ripped rotary knob 100 at the proximal end of a handgrip housing 102 via a preferably bidirectional Bowden connection (not shown). A self-retarding threading is located in the interior of the rotary knob 100, which converts the rotation of the rotary knob 100 into a translation of the Bowden cable. An overextension of the Bowden cable in both directions is prevented by stops in the mechanism of the rotary knob 100.

The movable element of the bidirectional Bowden connection is configured as a braided cable and a spiral tightly surrounding the cable, which is fixedly secured at least at both ends. The traction is transmitted through the cable, the thrust through the spiral. A rigid tube forms the outer sheath of the Bowden connection for guiding and receiving the counter forces.

Cross-sectional area is saved by the bidirectionality of the Bowden connection, because only one cable is required for straightening and bending the distal end, which is loaded under traction and thrust. The normal counter-cable used in deflectable endoscopes is not needed. Without the counter-cable, one has more freedom in the selection and distribution of other elements in the interior of the working shaft 92. Further, the pivot point of the deflecting members can be displaced asymmetrically from the center at a position lying opposed to the cable. This produces a larger lever action for the deflection and therefore a larger deflection force. At least one working channel or insert channel can be provided, as has been described with reference to FIG. 3 or to FIG. 1.

The treatment device 90 is introduced approximately up to the working position in the straight configuration. Introduction under visual control is possible with an inserted fiber optic probe, because the endoscope 96 is not provided with a straight ahead view. After reaching the approximate working position, the distal end is placed in its working position with the rotary knob 100, where the advantageous stiffening takes place at the end of the stop. A variation of the linkage 94 also provides a mechanism by which a stiffening of the flexible part 94 is possible in arbitrary deflection position through a further actuator element, without having to deflect entirely up to the stop.

When the proper deflection position is adjusted, the motor 22 can be activated and the endoscopic treatment on the surface can be carried out under simultaneous observation.

The treatment device 90 is preferably removed from the treatment area again in the straightened configuration. Analogously to the embodiment of FIG. 3, the endoscope 96 can be removed from the working shaft here for enlarged detail imaging of the surface by using the disassembled endoscope 96.

A modification of the embodiment shown in FIG. 4 consists of not using a rigid endoscope 96, but instead a fiber optics assembly which has a viewpoint from the end face of the deflectable distal end. The deflection mechanism and the additional working channel are configured analogously to the embodiment of FIG. 4.

A large variety of surface geometries can be treated with the three embodiments.

What is claimed is:

1. An exchangeable tool assembly for an endoscopic treatment device, comprising:
   a rotating tool adapted to contact and treat a surface;
   a coupling element for coupling said tool assembly to a motor of a treatment device;
   a flexible shaft having a distal end and a proximal end, said distal end being connected to said rotating tool and said proximal end being connected to said coupling element, said flexible shaft transmitting a rotary movement of said motor to said rotating tool in order to cause said rotating tool to rotate, said flexible shaft being connected to said rotating tool and said coupling element such that said flexible shaft and said rotating tool and said coupling element form a jointly exchangeable integral unit; and
   a locking mechanism for releasably holding said tool assembly at said treatment device, said locking mechanism comprising a locking element arranged at said rotating tool and a locking member arranged at said treatment device, which is engageable with said locking element to releasably hold said jointly exchangeable unit formed by said rotating tool and said flexible shaft and said coupling element, wherein said rotating tool, said flexible shaft and said coupling element are adapted to be withdrawn as an integral unit when the locking member arranged at said treatment device is disengaged from the locking element arranged at said rotating tool.

2. The tool assembly of claim 1, wherein said rotating tool comprises a working head and a tool shaft and wherein said locking element is configured as an annular groove in said tool shaft.

3. The tool assembly of claim 2, wherein a bearing bush is provided which receives an axial portion of said tool shaft and has a slot configured such that said locking element can pass through said slot.

4. The tool assembly of claim 1, wherein said flexible shaft is configured as a braided cable.

5. The tool assembly of claim 1, wherein said flexible shaft is configured as a hollow profile.

6. The tool assembly of claim 1, wherein said flexible shaft is made from a highly flexible alloy.

7. The tool assembly of claim 1, wherein a spiral is provided, which rotatably receives an axial portion of said flexible shaft.

8. The tool assembly of claim 7, wherein a mantle, preferably a plastic mantle, is provided surrounding the spiral.

9. An exchangeable tool assembly for an endoscopic treatment device, comprising:

a rotating tool adapted to contact and treat a surface;

a coupling element for coupling said tool assembly to a motor of a treatment device;

a flexible shaft having a distal end and a proximal end, said distal end being connected to said rotating tool and said proximal end being connected to said coupling element, said flexible shaft transmitting a rotary movement of said motor to said rotating tool, said flexible shaft being connected to said rotating tool such that said flexible shaft and said rotating tool form a jointly exchangeable unit; and a locking mechanism for releasably holding said tool assembly at said treatment device, said locking mechanism comprising a locking element arranged at said rotating tool and a locking member arranged at said treatment device, which is engageable with said locking element to releasably hold said jointly exchangeable unit formed by said rotating tool and said flexible shaft, which can be withdrawn as a whole when the locking member arranged at said treatment device is disengaged from the locking element arranged at said rotating tool, and a locking sleeve, at least part of which is slideable along said treatment device, such that, when said sleeve is in a first position, said sleeve urges said locking member into engagement with said locking element and, when said sleeve is in a second position, said locking member is disengaged from said locking element.

10. The tool assembly of claim 9, wherein said flexible shaft is also connected to said proximal coupling element such that said coupling element can be withdrawn together with said rotating tool and said flexible shaft after releasing said locking mechanism.

11. The tool assembly of claim 9, wherein said rotating tool comprises a working head and a tool shaft and wherein said locking element is configured as an annular groove in said tool shaft.

12. The tool assembly of claim 11, wherein a bearing bush is provided which receives an axial portion of said tool shaft and has a slot configured such that said locking element can pass through said slot.

13. The tool assembly of claim 9, wherein said flexible shaft is configured as a braided cable.

14. The tool assembly of claim 9, wherein said flexible shaft is configured as a hollow profile.

15. The tool assembly of claim 9, wherein said flexible shaft is made from a highly flexible alloy.

16. The tool assembly of claim 9, wherein a spiral is provided, which rotatably receives an axial portion of said flexible shaft.

17. The tool assembly of claim 16, wherein a mantle is provided surrounding the spiral.

* * * * *